US012674750B2

(12) United States Patent
Planat-Chretien

(10) Patent No.: US 12,674,750 B2
(45) Date of Patent: Jul. 7, 2026

(54) METHOD FOR ANALYSING AN OBJECT COMPRISING SEVERAL SUPERPOSED LAYERS, BY OPTICAL REFLECTANCE MEASUREMENTS

(71) Applicant: COMMISSARIAT A L'ENERGIE ATOMIQUE ET AUX ENERGIES ALTERNATIVES, Paris (FR)

(72) Inventor: Anne Planat-Chretien, Grenoble Cedex (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 231 days.

(21) Appl. No.: 18/397,385

(22) Filed: Dec. 27, 2023

(65) Prior Publication Data
US 2024/0210316 A1     Jun. 27, 2024

(30) Foreign Application Priority Data
Dec. 27, 2022    (FR) ..................................... 22 14565

(51) Int. Cl.
  *G01N 21/47*         (2006.01)
  *A61B 5/1455*        (2006.01)
  *G01N 21/49*         (2006.01)
(52) U.S. Cl.
  CPC ......... *G01N 21/47* (2013.01); *A61B 5/14553* (2013.01); *G01N 21/474* (2013.01);
  (Continued)
(58) Field of Classification Search
  CPC ...... G01N 21/47; G01N 21/474; G01N 21/49; G01N 2021/4709; G01N 2021/4742; A61B 5/14553
  See application file for complete search history.

(56) References Cited

U.S. PATENT DOCUMENTS 9,380,968 B2 * 7/2016 Nishida .............. A61B 5/14532
9,433,352 B2    9/2016 Niwayama et al.
  (Continued)

OTHER PUBLICATIONS

French Preliminary Search Report and Written Opinion issued Jul. 3, 2023 in French Application 22 14565 filed on Dec. 27, 2022, 10 pages (with English Translation of Categories of Cited Documents).

*Primary Examiner* — Dominic J Bologna
(74) *Attorney, Agent, or Firm* — Oblon, McClelland, Maier & Neustadt, L.L.P.

(57) ABSTRACT

Method for determining a variation of absorption properties of an object (20), between a first instant (t1) and a second instant (t2), the object comprising a surface layer (L1) and a deep layer (L2), the method comprising:

a) illumination of the object by a light source (10), emitting an illumination beam (11) forming a zone (12) on the surface of the object;

b) detection of photons backscattered by the object, the detected backscattered photons emanating from a detection zone ($14_1$, $14_2$, $14_3$), the detection zone being situated at a detection distance from the illumination zone, the detection distance being chosen from among, in ascending order:

a first detection distance (d1), forming a first detection zone;

a second detection distance (d2), forming a second detection zone;

a third detection distance (d3), forming a third detection zone.

8 Claims, 9 Drawing Sheets

(52) U.S. Cl.
CPC ..... *G01N 21/49* (2013.01); *G01N 2021/4709*
(2013.01); *G01N 2021/4742* (2013.01)

(56) References Cited

U.S. PATENT DOCUMENTS

| | | | |
|---|---|---|---|
| 11,147,481 B1 | 10/2021 | Kirby et al. | |
| 2007/0201788 A1* | 8/2007 | Liu ..................... | A61B 5/0059 |
| | | | 385/12 |
| 2014/0039284 A1* | 2/2014 | Niwayama ........... | A61B 5/0059 |
| | | | 600/324 |
| 2015/0015888 A1 | 1/2015 | Gulati et al. | |
| 2015/0018642 A1 | 1/2015 | Gulati et al. | |
| 2015/0018646 A1* | 1/2015 | Gulati .................. | A61B 5/1079 |
| | | | 600/322 |
| 2015/0041656 A1 | 2/2015 | Novotny et al. | |
| 2015/0045636 A1 | 2/2015 | Novotny et al. | |
| 2015/0119661 A1* | 4/2015 | Gilbert ................. | G01N 21/314 |
| | | | 600/316 |
| 2018/0180535 A1* | 6/2018 | Sorgato ............. | G01N 21/4795 |
| 2021/0204816 A1* | 7/2021 | Kirby ................... | G01J 1/4228 |

* cited by examiner $\mu_a\ cm^{-1}$ (cm)

METHOD FOR ANALYSING AN OBJECT COMPRISING SEVERAL SUPERPOSED LAYERS, BY OPTICAL REFLECTANCE MEASUREMENTS

TECHNICAL FIELD

The technical field of the invention relates to the analysis of an object comprising two superposed layers, by optical reflectance measurements.

PRIOR ART

Diffuse reflectance spectroscopy, usually referred to by the acronym DRS, is a non-destructive analysis technique that makes it possible to estimate light propagation properties in an object being analysed. This technique is for example described in EP2762064 or EP3054282 or EP3054281 or EP3311138. It consists in illuminating the medium by an incident light beam, and in detecting photons backscattered by the object being analysed, at a distance from the incident beam. The detection is frequently performed at different wavelengths and/or at several distances from the incident beam, so as to obtain spectral properties of light propagation in the object being analysed.

The light propagation properties generally comprise light absorption properties and/or light diffusion properties. These are notably absorption or diffusion coefficients, these respectively representing probabilities of absorption and of diffusion of a photon per unit of length. The estimation of the light propagation properties, at certain wavelengths, allows for an estimation of a concentration of analytes in the object being analysed. Thus, DRS can be used to estimate the concentrations of oxyhaemoglobin and deoxyhaemoglobin for example—making it possible to calculate the rate of oxygenation of the tissue and to estimate the total quantity of haemoglobin (oxyhaemoglobin+deoxyhaemoglobin).

One difficulty can occur when the object being analysed is not homogeneous and includes a surface layer under which there extends a deep layer. In order to correctly characterize the deep layer, the contribution of the surface layer must be taken into account under pain of inducing errors in the estimation of the concentrations of analytes of the deep layer. This is all the more so when the surface layer changes over time: the changes of the surface layer can be attributed to the deep layer (or vice versa), which can induce bad diagnoses; when it involves the extra-cerebral and cerebral compartment for example, a false negative in the case of cerebral hypoxia can have dramatic clinical and management consequences.

In the case of practical examination on the head of an individual, it is necessary to characterize, independently, a surface layer, corresponding to an extra-cerebral compartment (skin, cranium, dura mater, cerebrospinal fluid), and a deep layer, corresponding to the cortex. Such an independent characterization makes it possible to distinguish the occurrence of a systemic variation of optical properties, simultaneously affecting both layers, from the occurrence of a cerebral variation, affecting only the cortex.

The invention described hereinbelow addresses this issue: it involves separating the contributions of the surface and deep layers so as to estimate the change of concentrations, as a function of time, of an analyte in the two layers, the analyte notably being able to be oxyhaemoglobin or deoxyhaemoglobin.

SUMMARY OF THE INVENTION

A first subject of the invention is a method for determining a variation of absorption properties of an object, between a first instant and a second instant, later than the first instant, the object being delimited by a surface, the object comprising a surface layer and a deep layer, the surface layer extending between the surface and the deep layer, the method comprising:

a) illumination of the object by a light source, the light source emitting an illumination beam forming an illumination zone on the surface of the object;

b) detection of photons backscattered by the object, after being propagated in the object, by a photodetector, the detected backscattered photons emanating from a detection zone on the surface of the object, the detection zone being situated at a detection distance from the illumination zone, the detection distance being chosen from among, in ascending order:

a first detection distance, forming a first detection zone;

a second detection distance, forming a second detection zone;

a third detection distance, forming a third detection zone;

the detection of the photons generating a detection signal;

wherein the method comprises, chronologically, the following steps:

(i): at the first instant, implementation of the steps a) and b) by detecting, in the step b), the photons backscattered in the second and third detection zones;

(ii): from the detection signals resulting from (i):

taking into account an optical property of diffusion in the object;

estimating of an absorption coefficient of the object, the surface layer and the deep layer being considered as having the same absorption coefficient;

(iii): from the absorption coefficient resulting from (ii), estimation of an average distance travelled by the photons, in the surface layer, between the illumination zone and the first detection zone;

(iv): at the second instant, implementation of the steps a) and b) by detecting, in the step b), the photons backscattered in the first detection zone;

(v): from the detection signal resulting from (iv), and the average distance resulting from (iii), estimation of a variation of the absorption coefficient in the surface layer between the first instant and the second instant;

(vi): at the second instant, implementation of the steps a) and b) by detecting, in the step b), the photons backscattered in the second and third detection zones;

(vii): from the detection signals resulting from (vi), and the variation of the absorption coefficient in the surface layer, resulting from (v), estimation of the absorption coefficient in the deep layer at the second instant.

The step (i) can comprise:

from the detection signals measured in the second detection zone and the third detection zone, at the first instant, determination of a spatial variation of the absorbance of the object, at the first instant;

from the spatial variation of the absorbance of the object, at the first instant, first estimation of the absorption coefficient in the surface layer and in the deep layer at the first instant;

application of a first absorption calibration function to the first estimation of the absorption coefficient resulting from the preceding substep, so as to determine the absorption coefficient, in the surface layer and in the deep layer, at the first instant.

The step (vii) can comprise:

from the detection signals measured in the second detection zone and the third detection zone, at the second instant, determination of a spatial variation of the absorbance of the object, at the second instant;

from the spatial variation of the absorbance of the object, at the second instant, first estimation of the absorption coefficient in the deep layer at the second instant;

application of a second absorption calibration function to the first estimation of the absorption coefficient resulting from the preceding substep, so as to determine the absorption coefficient, in the deep layer, at the second instant, the second absorption calibration function taking into account the variation of the absorption coefficient in the surface layer between the first instant and the second instant.

The step (vii) can comprise:

from the variation of the absorption coefficient in the surface layer resulting from (v), estimation of an average distance travelled by the photons, in the surface layer, between the illumination zone and the first detection zone, at the second instant;

calculation of a ratio between the average distances travelled by the photons resulting respectively from the preceding substep and the step (ii);

use of the ratio to form the second absorption calibration function.

According to one possibility, the method comprises an estimation of the absorption coefficient, in the surface layer, at the second instant;

the second absorption calibration function is established using modellings or experimental measurements performed on phantoms, each phantom comprising:

a surface layer, the absorption coefficient of which corresponds to the absorption coefficient estimated, in the surface layer, at the second instant;

a deep layer, the absorption coefficient of which is variable between the different phantoms.

According to one possibility, the first detection distance is less than 2 cm;

the second and third detection distances are greater than 2 cm.

A second subject of the invention is a device intended to be applied facing a surface of an object between at least one first instant and a second instant, the device comprising:

a light source configured to emit an illumination beam, forming an illumination zone, on the surface of the object;

a photodetector, configured to form a detection signal from a detection of photons backscattered by the object, in;

a first detection zone, extending to a first detection distance from the illumination zone;

a second detection zone, extending to a second detection distance from the illumination zone, the second detection distance being greater than the first detection distance;

a third detection zone, extending to a third detection distance from the illumination zone, the third detection distance being greater than the second detection distance;

a processing unit, programmed to implement the steps (ii), (iii), (v) and (vii) of a method according to the first subject of the invention from detection signals formed by the photodetector:

in the step (ii), from photons detected in the second and third detection zones;

in the step (v), from photons detected in the first detection zone;

in the step (vii), from photons detected in the second and third detection zones.

The first detection distance can be less than 2 cm. The second and third detection distances can be greater than 2 cm.

The invention will be better understood on reading the explanation of the examples of embodiments presented, hereinafter in the description, in association with the figures listed hereinbelow.

FIGURES

FIG. 1A schematically represents a device allowing an implementation of the invention.

EXPLANATION OF PARTICULAR EMBODIMENTS

Figure 1A:
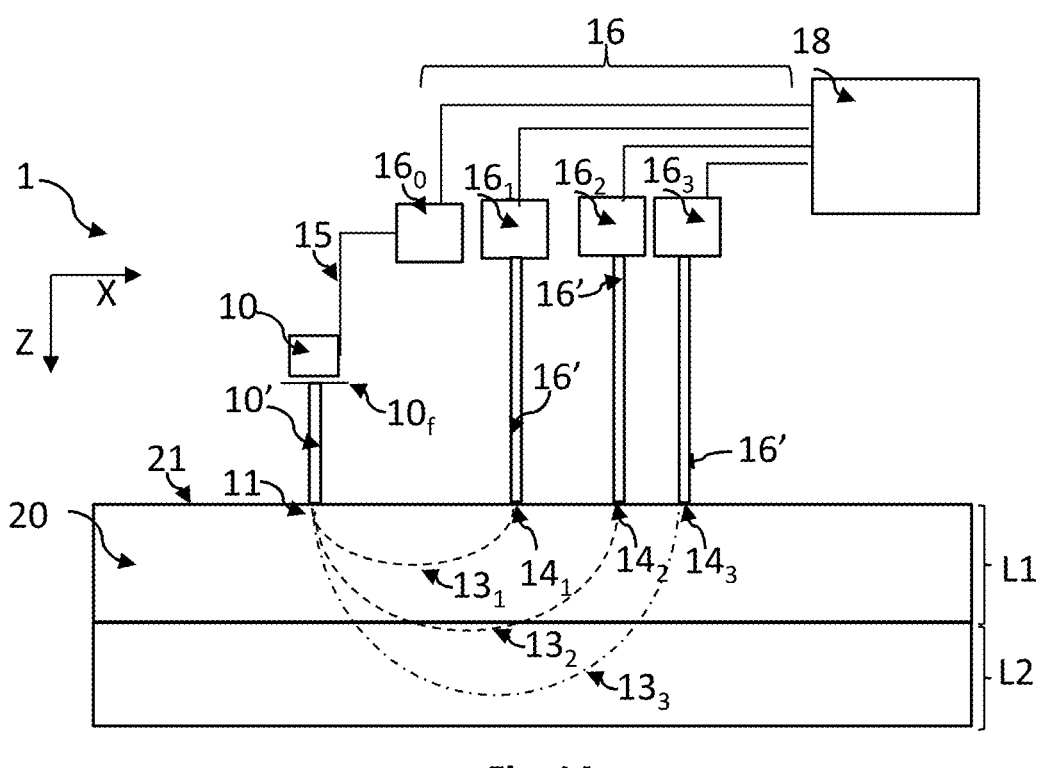
FIG. 1B shows an illumination zone and a detection zone formed on the surface of a sample.

FIG. 1A represents a device 1 configured to estimate optical properties of absorption in an object 20. In this example, the object is a biological tissue, for example a part of the head of an individual, animal or human being.

Figure 1B:
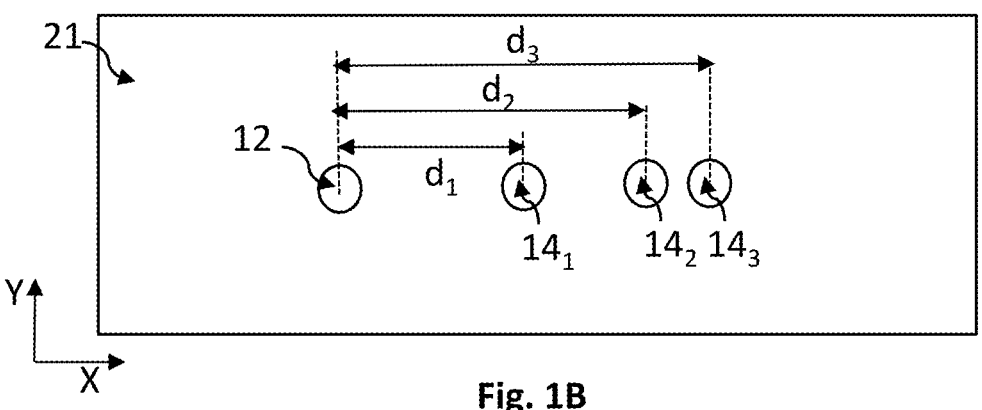

The device comprises a light source 10. The light source is configured to emit a light beam 11, being propagated towards the object 20 to be analysed. The sample 20 is delimited by a surface 21. The intersection of the illumination beam 11 and of the surface 21 of the sample forms an illumination zone 12 that is spatially delimited. The illumination zone is preferably a spot zone: it for example is inscribed in a circle of a diameter less than 1 mm, even less than a few hundreds of μm, for example 100 μm or 1 mm. The elementary illumination zone 12 is represented in FIG. 1B.

The light source can be disposed in contact with the object 20 or at a distance therefrom. The light source can be a laser, an LED or OLED (or any other source of photons). In the example represented, the light source is disposed at a distance from the sample. The light beam 11 is transported to the surface 21 of the sample by an illumination optical fibre 10'. The light source can be filtered in wavelength by a filter $10_f$.

The photons forming the illumination beam 11 are propagated in the biological tissue to be analysed. The biological tissue 20 is formed by a diffusing medium, susceptible to absorbing photons, the propagation properties of the photons in the medium depending notably on absorption or diffusion properties in the medium. Normally, the absorption properties can be quantified by a linear absorption coefficient $\mu_a(\lambda)$. As is known, the linear absorption coefficient quantifies a probability of absorption by the medium per unit of length, at the wavelength $\lambda$. It is usually expressed in $cm^{-1}$. The diffusion properties can be quantified by a diffusion coefficient $\mu_s(\lambda)$ or a reduced diffusion coefficient $\mu_s'(\lambda)$, which quantify a probability of diffusion by the medium per unit of length, at the wavelength $\lambda$. It is usually expressed in $cm^{-1}$.

The device comprises at least three elementary photodetectors 161, 162, 163 forming a photodetector 16. The photons detected by the photodetector 16 emanate from an elementary detection zone 14 on the surface 21 of the sample 20. The detection zone 14 is preferably a spot zone, by being, like the illumination zone 12, inscribed in a diameter less than 1 mm even 250 μm. The detection zone 14 is separated from the illumination zone 12. The distance between the illumination zone 12 and the detection zone 14 is a detection distance d. It can be a few centimetres or of the order of a centimetre, and can even be less than 1 cm.

Each photodetector can be one or more pixels of an image sensor, a photon counter, an organic photodetector, a photodiode (or any other component allowing the detection of photons).

The device is configured to form:

a first detection zone 14₁, extending to a first detection distance d1 from the illumination zone;

a second detection zone 14₂, extending to a second detection distance d2 from the illumination zone, the second detection distance being greater than the first detection distance;

a third detection zone 14₃, extending to a third detection distance d3 from the illumination zone, the third detection distance being greater than the second detection distance.

According to one possibility, the number of detection zones can be greater than 3, particularly when the number of layers to be characterized is greater than 2.

In the case of a study on the head of a foetus or of a child, the first distance d1 can be less than 1 cm. The second and third distances can be greater than 1 cm, for example d2=2.25 cm and d3=2.5 cm.

In the case of a head of an adult, the first distance d1 can be of the order of 1 cm. The second and third distances can be greater than or equal to 3 cm, for example d2=3 cm and d3=3.5 cm.

The choice of the distances d1, d2 and d3 depends on the thickness of the surface layer. The first distance d1 is defined such that the photons backscattered in the first detection zone have essentially passed through the surface layer. The distances d2 and d3 are chosen such that the majority of the detected photons have passed through the deep layer. It is understood that these distances are defined on a per-case basis, according to the geometry and the optical properties of the object to be characterized. These distances depend therefore on the optical properties and on the thickness of the surface layer.

In FIG. 1B, the paths 13₁, 13₂ and 13₃ correspond to average paths travelled by the photons respectively detected in the detection zones 14₁, 14₂, 14₃.

In the embodiment of the invention, the light source emits according to an illumination wavelength that can correspond to a wavelength of absorption of deoxyhaemoglobin ($\lambda$=750 nm) and/or of oxyhaemoglobin ($\lambda$=850 nm). That makes it possible to estimate deoxyhaemoglobin and oxyhaemoglobin concentrations from the measured absorption coefficients, according to relationships known to the person skilled in the art.

The device comprises a processing unit 18. The processing unit comprises a microprocessor programmed to implement the steps described hereinbelow, in association with FIG. 2, from detection signals detected by the photodetector following an illumination of the object by the light source.

The device is applied against the surface 21 of an object 20, the latter comprising a surface layer L1 and a deep layer L2. The surface layer is interposed between the surface of the object and the deep layer. A layer is understood to be a macroscopic part of the sample in which the optical properties are considered to be homogeneous.

The object 20 can for example be an organ, such as a head. In this case, the surface layer 21 corresponds to an extra-cerebral layer (skin+fat+cranium+dura mater+cerebrospinal fluid) and the deep layer corresponds to a cerebral layer (cortex).

It is known that, by using detection signals detected in different detection zones, it is possible to estimate the optical properties, in particular the absorption coefficient, of an object.

For example, the diffuse reflectance spectroscopy technique (SRS—Spatially Resolved Spectroscopy), is a "multi-distance" approach, which makes it possible to estimate an absorption coefficient, for example to determine an oxygen saturation level.

Generally, each reflectance measurement consists in measuring the signal backscattered by the medium, emanating from a detection zone situated at a detection distance from the illumination zone. A detection signal $S(d,\lambda,t)$ is thus obtained, that is dependent on the number of photons backscattered at the detection distance. The detection signal is measured by the photodetector. It is however a raw detection signal, that should preferably be corrected.

A first correction consists in correcting the offset (dark current) of the instrument, according to the expression:

$$S_c(d,\lambda,t)=S(d,\lambda,t)-S_{offset}(\lambda) \tag{1}$$

in which $S_{offset}(\lambda)$ is a dark signal, detected while the source is off. That corresponds to the detection noise associated with the measurement chain.

A second correction consists in taking into account a potential drift of the light source 10, forming the illumination zone. This entails taking into account a variation of the quantity of photons forming the illumination beam. For that, an excitation return fibre directly links the light source to a photodetector 16₀. The photodetector is thus configured to measure the quantity of light forming the illumination beam $S_{c,0}(\lambda,t)$.

The reflectance corresponds to a ratio between $S_c(d,\lambda,t)$ and $S_{c,0}(\lambda,t)$ explained according to the expression:

$$R(d,\lambda,t) = \frac{S_c(d,\lambda,t)}{S_{c,0}(\lambda,t)} \tag{2}$$

The absorbance of the object, at the detection distance d, is obtained according to the expression:

$$A(d,\lambda,t)=DO=-\log_{10}(R(d,\lambda,t)) \tag{3}$$

According to the "multi-distance" approach, detection signals are available, measured according to different detection distances, for example d and d'. Thus, just as many estimations of the absorbance are obtained, at each detection distance. The coefficients $\mu_a$ and $\mu'_s$ are linked to the absorbance by the relationship:

$$\mu_a \mu'_s \approx \frac{1}{3}\left(\ln(10)\frac{\partial A}{\partial d} - \frac{2}{d}\right)^2 \qquad (4)$$

with $$\frac{\partial A}{\partial d} \sim \frac{\Delta A}{\Delta d} = \frac{A(d, \lambda, t1) - A(d', \lambda, t1)}{d - d'} \qquad (5)$$

If one of the coefficients is known, for example $\mu'_s$, $\mu_a$ can be deduced from (4) and (5).

Such an approach is suitable when the object being analysed is considered as homogeneous. On a non-homogeneous object, comprising a surface layer and a deep layer, this approach can be applied to determine the $\mu_a$ of the deep layer, subject to the surface layer being sufficiently fine, typically less than 0.5 cm or 0.6 cm and the distances d2 and d3 being sufficiently great. In this case, the spatial variation of the absorbance $\Delta A$ makes it possible to dispense with the contribution of the surface layer, considered as identical in d2 and d3. In practice (example of the head of a child/adult), this correction does not make it possible to dispense totally with the contribution of the surface layer (see example described in association with FIGS. 5A to 5D).

According to another approach, called MBL (Modified Beer Lambert), the absorption coefficient can be estimated, from an absorbance A(d) estimated according to a detection distance d, by $$A(d) = \frac{1}{\ln(10)}(\mu_a dDPF + G), \qquad (6)$$

in which DPF is an average path travelled in the object, by the photons forming the detection signal.

G is a constant dependent on the diffusion of the medium and on the geometry of the device. The constant G can be eliminated by determining a temporal variation of the absorbance $\Delta A(t1,t2)$ between two instants t1 and t2.

$$\Delta A(t1, t2) = \frac{1}{\ln(10)}d1DPF\Delta\mu_a(L1, t1, t2) \qquad (7)$$

In which $\Delta\mu_a(L1,t1,t2)$ corresponds to a variation of $\mu_a(L1)$ between the instants t1 and t2 in the surface layer L1.

The MBL method has already been implemented by combining a short detection distance and a long detection distance, so as to correct the contribution of the surface layer in the estimation of the absorption of a deep layer. However, it has been shown that this method has limitations, in particular when the temporal variations of the absorption coefficient are of the same type in the deep layer and in the surface layer. In such a situation, the deep layer can be "over-corrected" by the surface layer. This means that a variation of the absorption in the deep layer may be masked. Thus, in the case of occurrence of a hypoxia in the surface layer and the deep layer, the hypoxia of the deep layer can be under-estimated, even not detected.

The MBL approach associated with the short distance does however make it possible to characterize the surface layer of the object.

Figure 2:
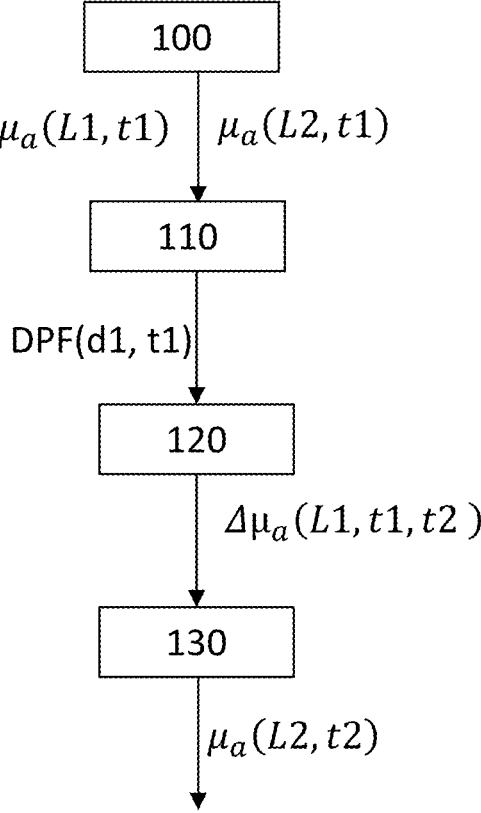
FIG. 2 shows the main steps allowing an implementation of the invention.

FIG. 2 illustrates the main steps of the invention. The device used makes it possible to combine the two approaches previously described (SRS and MBL) by recourse to a first low detection distance (i.e. generally <1 cm) and two higher detection distances (2 cm>d2>d3). That makes it possible to combine the SRS method by implementing the detection signals detected at the detection distances d2 and d3, and MBL, by implementing a signal detected at a detection distance d1.

Step 100: initialization. This step is performed at a first instant t1.

During a step 100, a hypothesis is taken into account whereby the object is homogeneous: the surface layer and the deep layer are considered to exhibit the same optical diffusion and absorption properties.

A reduced diffusion coefficient $\mu s'$ determined a priori is taken into account. The document EP3054281 describes a method that makes it possible to determine the reduced diffusion coefficient of a medium. Analytical empirical models can be used.

During this step, a measurement of the reflectance is performed according to two high detection distances, that is to say the second distance d2 and the third distance d3.

From the detected signals S(d2,λ,t1) and S(d3,λ,t1), the expressions (1) to (3) are implemented to obtain absorbances A(d2,λ,t1) and A(d3,λ,t1).

$$\mu_a(\widetilde{L1}, t1)\mu'_s = \mu_a(\widetilde{L2}, t1)\mu'_s \approx \frac{1}{3}\left(\ln(10)\frac{\partial A}{\partial d} - \frac{2}{d}\right)^2, \qquad (10)$$

with $$\frac{\partial A}{\partial d} \sim \frac{\Delta A}{\Delta d} = \frac{A(d3, \lambda, t1) - A(d2, \lambda, t1)}{d3 - d2}, \qquad (11)$$

derived from (5)

$\mu_a(\widetilde{L1}, t1)$ is a first-order estimation of the absorption coefficient $\mu_a(L1,t1)$ of the surface layer L1, at the instant t1;

$\mu_a(\widetilde{L2}, t1)$ is a first-order estimation of the absorption coefficient $\mu_a(L2,t1)$ of the deep layer L2, at the instant t1;

By hypothesis: $\mu_a(L1,t1)=\mu_a(L2,t1)$ $\mu_a(\widetilde{L1}, t1)$ and $\mu_a(\widetilde{L2}, t1)$ are deduced from the expression (10) given that $\mu'_s$ is known.

$\mu_a(L1,t1)$ and $\mu_a(L2,t1)$ are deduced from $\mu_a(\widetilde{L2}, t1)$ and $\mu_a(\widetilde{L2}, t1)$ by taking into account a first absorption calibration function, established on the basis of modellings and/or of calibration phantoms by taking into account known coefficients $\mu_a$ and $\mu'_s$. The absorption calibration function makes it possible to take into account the instrument response, in particular when known phantoms are used, or if the instrument response is taken into account in the modelling.

Figure 3:
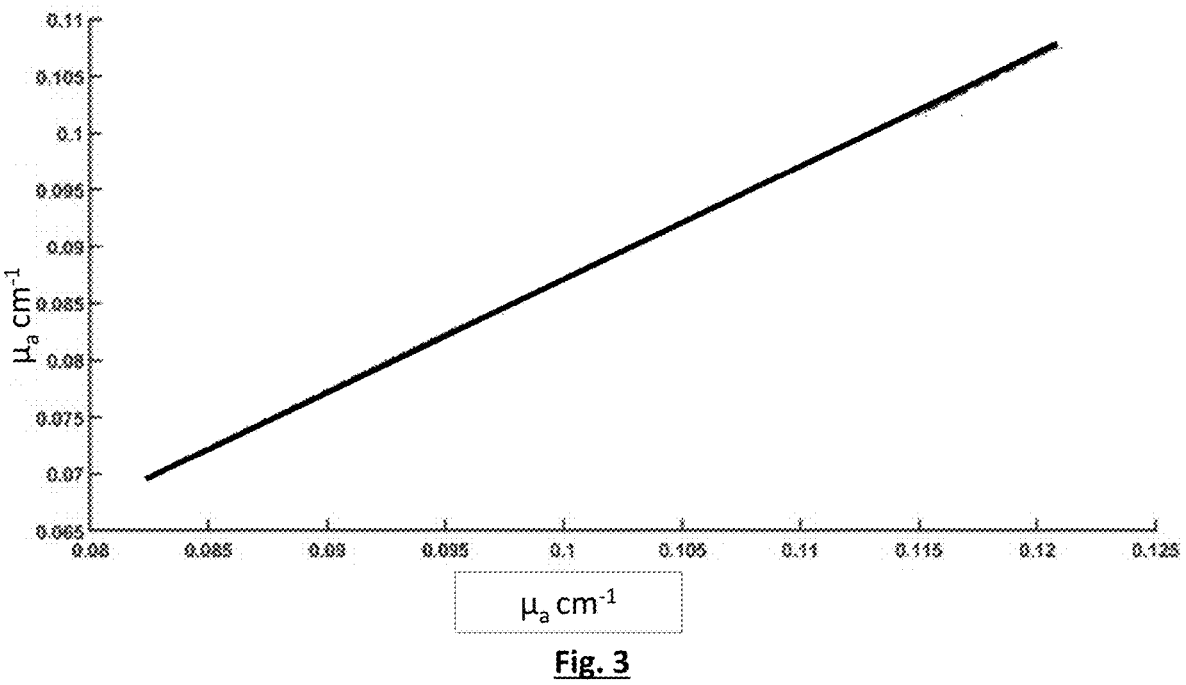
FIG. 3 represents an example of absorption calibration function.

FIG. 3 illustrates an example of linear absorption calibration function, of the following type:

$$\mu_a = a_0\widetilde{\mu_a} + b_0 \qquad (12).$$

By applying this function to $\mu_a(\widetilde{L2},t1)$ (or to $\mu_a(\widetilde{L2},t1)$), $\mu_a$ (L1,t1) and $\mu_a$(L2,t1) are obtained.

In FIG. 3, the Y axis corresponds to the true value $\mu_a$ and the X axis corresponds to the value $\widetilde{\mu_a}$ resulting from the combination of the expressions (10) and (11), from detection signals measured on homogeneous or modelled phantoms. A homogeneous phantom is understood to be a phantom whose optical properties are homogeneous. The scalars $a_0$ and $b_0$ are parameters of the absorption calibration function.

Following the step 100, there is available an estimation of the coefficient $\mu_a$ of the surface layer L1 and of the deep layer L2 at the instant t1.

Step 110: evaluation of the average path of the photons in the surface layer, at the instant t1.

During this step, the average path travelled by the photons in the surface layer, between the illumination zone and the detection zone corresponding to a low detection distance, that is to say the first detection distance d1, is determined. The first detection distance d1 is chosen such that the photons detected at this distance are essentially representative of the surface layer. In FIG. 1B, the average path $13_1$ of the photons detected at the first detection distance has been represented.

The average path, denoted DPF (acronym for Differential Pathlength Factor), travelled can be estimated, as a first approximation, according to the expression:

$$\widetilde{DPF}(d1,t1) = \frac{1}{2}\left(\frac{3\mu_s'}{\mu_a(L1,t1)}\right)^{1/2}\left(1-\left(\frac{1}{1+d1(3\mu_a(L1,t1)\mu_s')^{1/2}}\right)\right)$$ (13)

The expression (13) has been described in Scholkmann, F., & Wolf, M. General equation for the differential pathlength factor of the frontal human head depending on wavelength and age, 2013.

However, the analytical expression (13) is valid for great detection distances, typically greater than 1 cm or 2 cm. Now, the first detection distance is generally less than 1 cm. For lesser detection distances, it is possible to apply a correction factor k, such that DPF(d1,t1)=k×$\widetilde{DPF}$(d1,t1) (14)

Figure 4:
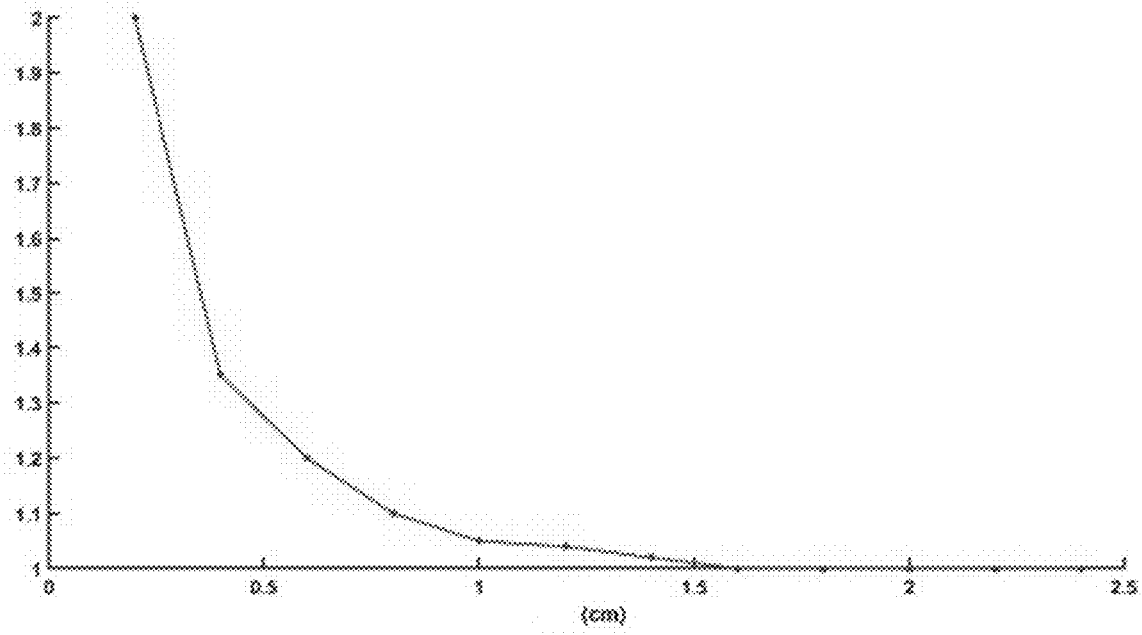
FIG. 4 shows an example of determination of a correction function.

FIG. 4 shows the trend of the realignment factor (Y axis) as a function of detection distance (X axis—unit cm). The curve of FIG. 4 was obtained by simulations.

Step 120: determination of a variation of the absorption coefficient of the surface layer at an instant t2.

The step 120 is implemented at a second instant t2, later than the instant t1. The instant t2 can be later by a few minutes or a few tens of minutes or a few hours than the instant t1.

During this step, by using the DPF(d1,t1) resulting from the step 110, the absorption coefficient of the first layer, at the instant t2, is determined according to the expression:

$$A(d1,t2) = \frac{1}{\ln(10)}(\mu_a(d1)d1DPF(d1,t1)+G)$$ (15)

As previously described, in association with (6), the constant G can be eliminated by determining a variation of the absorbance $\Delta A(t1,t2)$ between the instants t1 and t2.

$$\Delta A(t1,t2) = \frac{1}{\ln(10)}d1DPF\Delta\mu_a(L1,t1,t2)$$ (16)

In which $\Delta\mu_a$(L1,t1,t2) corresponds to a variation of $\mu_a$(L1) between the instants t1 and t2 in the surface layer L1.

The implementation of the expressions (15) and (16) assumes that the variation of the DPF is considered to be negligible between the instants t1 and t2.

Step 130: updating the absorption coefficient of the deep layer at the instant t2.

This step aims to take into account the variation of the absorption coefficient, in the surface layer, to estimate the absorption coefficient in the deep layer at the instant t2.

As in the step 100, a measurement of the reflectance is performed at the backscattering distances d2 and d3.

Thus, $$\mu_a(\widetilde{L2},t2)\mu_s' \approx \frac{1}{3}\left(\ln(10)\frac{\partial A}{\partial d}-\frac{2}{d}\right)^2$$ (17)

with $$\frac{\partial A}{\partial d} \sim \frac{\Delta A}{\Delta d} = \frac{A(d3,\lambda,t2)-A(d2,\lambda,t2)}{d3-d2}$$ (18)

The expression (17) makes it possible to obtain $\mu_a(\widetilde{L2},t2)$, which is a first-order estimation of the absorption coefficient $\mu_a$(L2,t2) in the deep layer L2 at the instant t2.

According to the same approach as described in the step 110, the recourse to an absorption calibration function, called second absorption calibration function, taking into account the instrument response, is necessary in order to determine $\mu_a$(L2,t2). An important aspect of the invention is to take into account the absorption in the surface layer which can be different from the absorption in the deep layer (two-layer model) to establish the second absorption calibration function.

At the instant t1, the calibration function is linear, of the following type $\mu_a$(L2,t1)=fa$_0\mu_a(\widetilde{L2},t1)$+c$_0$ (19) in which f and c$_0$ are scalars.

The parameters fa$_0$ and c$_0$ are determined on the basis of modellings and/or measurements performed on two-layer phantoms, comprising a surface layer, the absorption coefficient of which is $\mu_a$(L1,t1), and a deep layer of the same thickness as the object being analysed, and preferably the same diffusion properties.

Now, according to (12), $\mu_a$(L2,t1)=a$_0\mu_a(\widetilde{L2},t1)$+b$_0$ (20)

By combining (19) and (20), the following is obtained:

$\mu_a$(L2,t1)=fa$_0\mu_a(\widetilde{L2},t1)$+(1−f)$\mu_a(\widetilde{L2},t1)$+b$_0$ (21)

The expression (21) is an analytical expression, corresponding to an absorption calibration function, at the instant t1, that makes it possible to determine $\mu_a$(L2,t1) from $\mu_a(\widetilde{L2},t1)$, according to a two-layer model. If it is established from experimental tests, it takes into account the instrument response. Otherwise, it is preferable to introduce the instrument response in the modelling.

At the instant t2, the expression (21) must be corrected, so as to take into account the trend of $\mu_a$(L1) between the instants t1 and t2.

At the instant t2, the absorption calibration function becomes:

$\mu_a$(L2,t2)=gfa$_0\mu_a(\widetilde{L2},t2)$+(1−f)$\mu_a(\widetilde{L2},t2)$+b$_0$ (21)

With $$g = \frac{\overline{DPF}(d1, t2)}{\overline{DPF}(d1, t1)},$$

with $$\overline{DPF}(d1, t1) = \frac{1}{2}\left(\frac{3\mu_s'}{\mu_a(L1, t1)}\right)^{1/2}\left(1 - \left(\frac{1}{1 + d1(3\mu_a(L1, t1)\mu_s')^{1/2}}\right)\right) \quad (22)$$

$$\overline{DPF}(d1, t2) = \frac{1}{2}\left(\frac{3\mu_s'}{\mu_a(L1, t2)}\right)^{1/2}\left(1 - \left(\frac{1}{1 + d1(3\mu_a(L1, t2)\mu_s')^{1/2}}\right)\right) \quad (23)$$

The term g reflects the fact that the trend of the absorption in the surface layer between the instants t1 and t2 has been taken into account.

Thus, from $\mu_a(\widehat{L2}, t2)$ resulting from (17), (21) is applied, so as to estimate $\mu_a(L2,t2)$, the variation of $\mu_a(L1)$, between the instants t1 and t2, in the surface layer L1 being taken into account in the multiplying term g.

According to another possibility, a correction function of the following type is determined:

$$\mu_a(L2,t2) = a'_0\mu_a(\widehat{L2}, t2) + b'_0 \quad (24)$$

$a'_0$ and $b'_0$ being determined from modellings and experimental measurements on two-layer phantoms, the $\mu_a$ of the deep layer being variable, the surface layer having an absorption coefficient $\mu_a(L1,t2)$, such that:

$$\mu_a(L1,t2) = \mu_a(L1,t1) + \Delta\mu_a(L1,t1,t2) \quad (25)$$

EXPERIMENTAL TESTS

An implementation of the invention was simulated in different configurations. In the test configurations, a biological tissue was taken into account, comprising a surface layer, 0.5 mm thick, together with a deep layer and the reduced diffusion coefficient of which was 9.35 $cm^{-1}$ at $\lambda$=750 nm and 7.64 $cm^{-1}$ at $\lambda$=850 nm. Different temporal profiles of the oxygenation rate (TOI) of the surface layer end of the deep layer were simulated. TOI is a tissue oxygenation index, such as:

$$TOI = \frac{[HbO2]}{[HbO2] + [Hb]} \times 100 \quad (26)$$

[HbO2] corresponds to the oxyhaemoglobin concentration

[Hb] corresponds to the deoxyhaemoglobin concentration.

The invention was implemented at a first instant, which corresponds to t=0, then at different successive instants, up to t=60. The instant t1 corresponds to the first instant. The instants t2 correspond to each measurement instant up to t=60. The simulated measurements were subjected to added noise: Poisson-type photonic noise and instrument noise of Gaussian type.

The invention was implemented to evaluate the absorption coefficient Pa, at $\lambda$=750 nm and at $\lambda$=850 nm, over time, in the surface layer and in the deep layer. From Pa, in the surface layer and in the deep layer, [HbO2] and [Hb] were estimated in each of these layers.

Figure 5A:
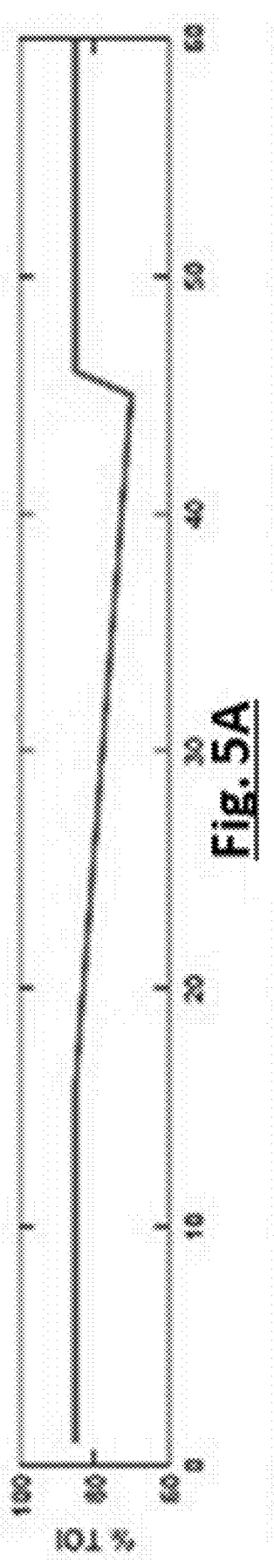
FIGS. 5A to 5D show results obtained, by simulation, by implementing the invention according to a first configuration.
Figure 5B:
Figure 5C:
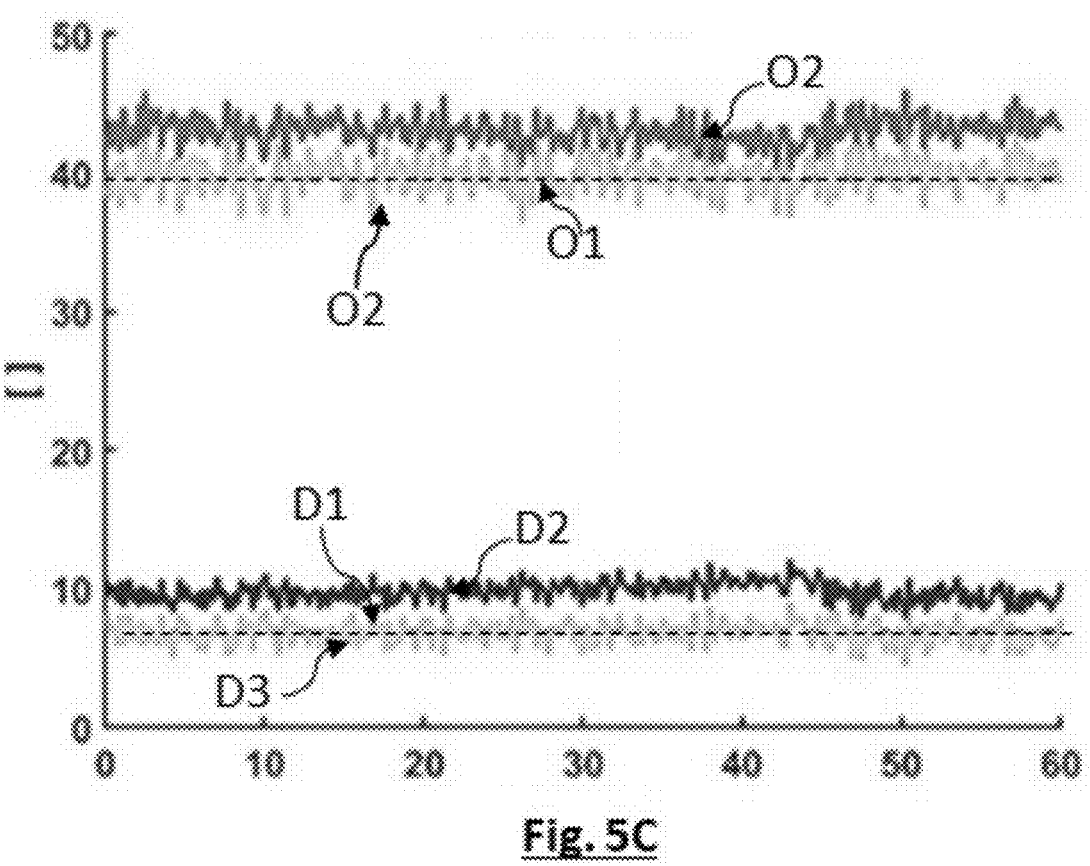
Figure 5D:
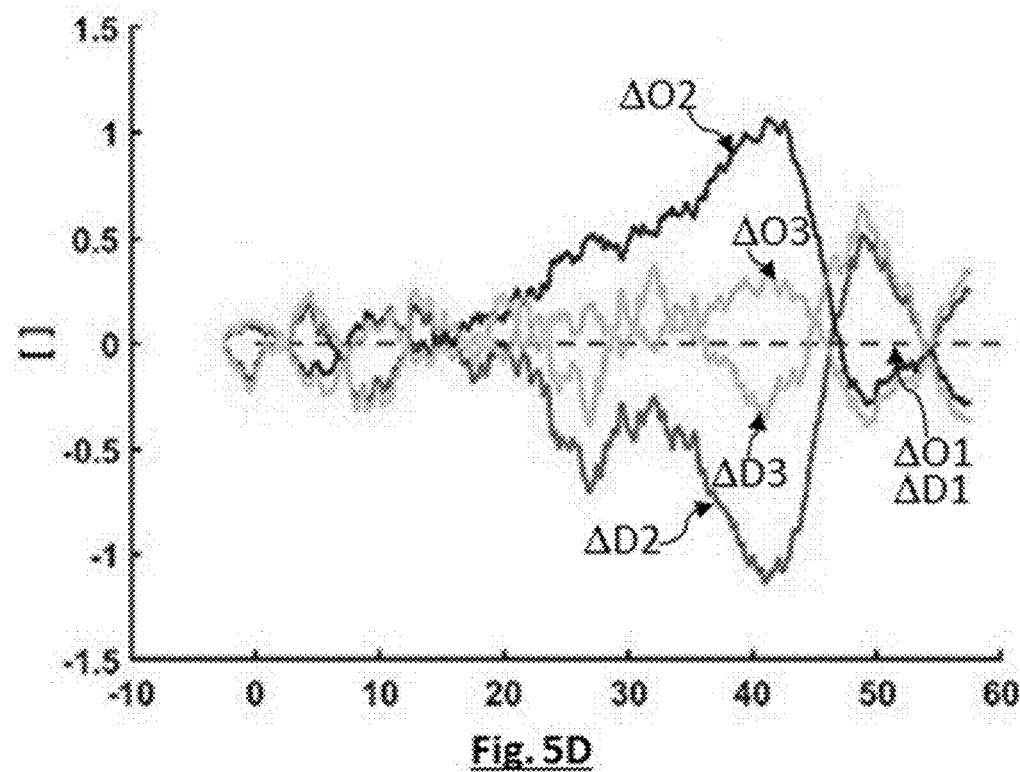

According to a first configuration, see FIGS. 5A to 5D, the oxygenation of the surface layer varies (see FIG. 5A), while the oxygenation of the deep layer is constant (see FIG. 5B). In FIGS. 5A and 5B, the X axis corresponds to the time (arbitrary unit) and the Y axis corresponds to the oxygenation rate defined in (26).

FIG. 5C shows:

the real profile of [HbO2] in the deep layer: see curve O1 the estimations of [HbO2] in the deep layer without taking into account the variation of pa in the surface layer by SRS: see curve O2 the estimations of [HbO2] in the deep layer by implementing the invention: see curve O3 the real profile of [Hb] in the deep layer: see curve D1 the estimations of [Hb] in the deep layer without taking into account the variation of pa in the surface layer (SRS method in this example): see curve D2 the estimations of [Hb] in the deep layer by implementing the invention: see curve D3.

It can be seen that the curves D3 and O3 are closer to the real values D1 and O1.

FIG. 5D shows:

the real variation [HbO2] in the deep layer: see curve $\Delta$O1 the estimations of the variation of [HbO2] in the deep layer without taking into account the variation of pa in the surface layer: see curve $\Delta$O2 the estimations of the variation of [HbO2] in the deep layer by implementing the invention: see curve $\Delta$O3 the real variation of [Hb] in the deep layer: see curve $\Delta$D1 the estimations of the variation of [Hb] in the deep layer without taking into account the variation of pa in the surface layer: see curve $\Delta$D2 the estimations of the variation of [Hb] in the deep layer by implementing the invention: see curve $\Delta$D3.

It can be seen that the curves $\Delta$D3 and $\Delta$O3 are closer to the real values $\Delta$D1 and $\Delta$O1.

Figure 6A:
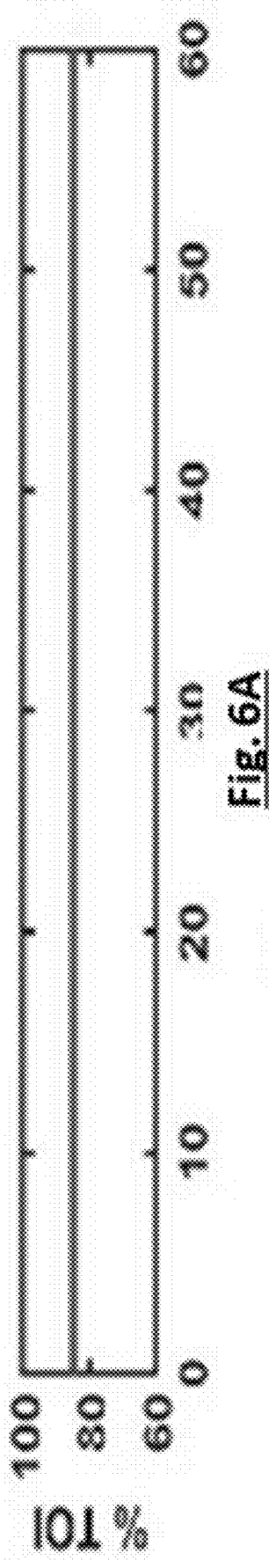
FIGS. 6A to 6D show results obtained, by simulation, by implementing the invention according to a second configuration.
Figure 6B:
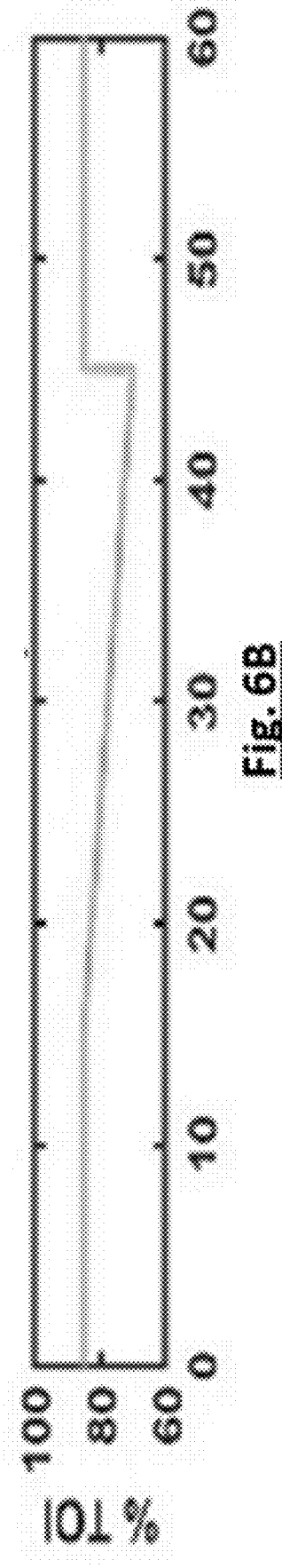

According to a second configuration, see FIGS. 6A to 6D, the oxygenation of the surface layer is stable (see FIG. 6A), while the oxygenation of the deep layer varies (see FIG. 6B). In FIGS. 6A and 6B, the X axis corresponds to the time (arbitrary unit) and the Y axis corresponds to the oxygenation rate defined in (26).

FIG. 6C shows:

the real profile of [HbO2] in the deep layer: see curve O1 the estimations of [HbO2] in the deep layer without taking into account the variation of pa in the surface layer: see curve O2 the estimations of [HbO2] in the deep layer by implementing the invention: see curve O3 the real profile of [Hb] in the deep layer: see curve D1 the estimations of [Hb] in the deep layer without taking into account the variation of pa in the surface layer: see curve D2 the estimations of [Hb] in the deep layer by implementing the invention: see curve D3.

Figure 6C:
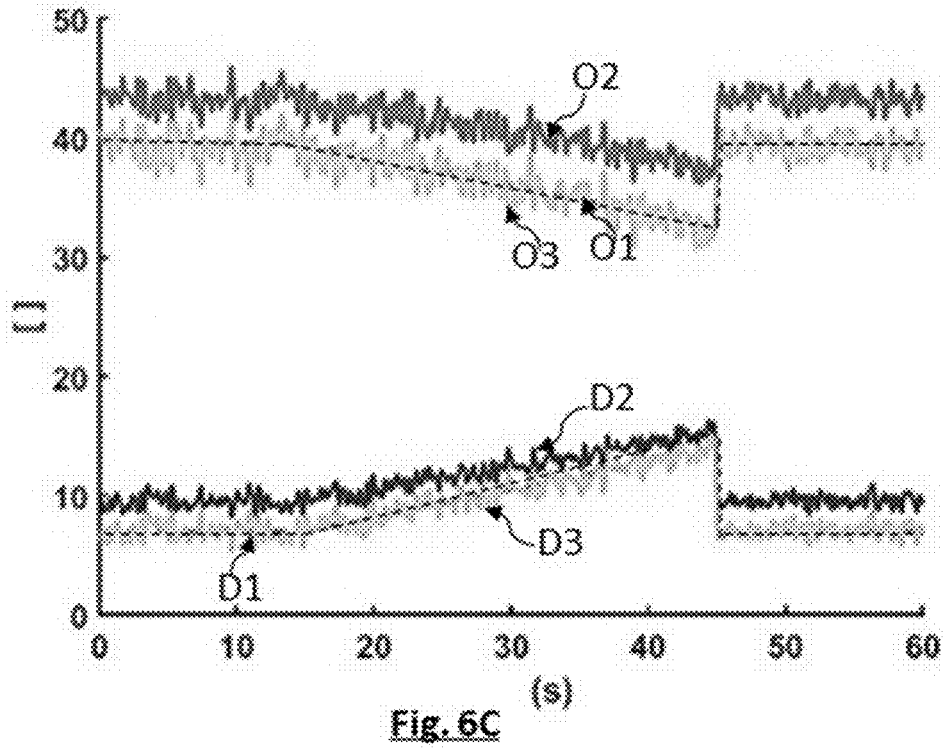

In FIG. 6C, the X axis corresponds to the time (arbitrary unit) and the Y axis corresponds to the estimated concentrations.

It can be seen that the curves D3 and O3 are closer to the real values D1 and O1. That is due to the fact that the invention allows for a better control of the concentration of Hb or HbO2 in the surface layer. More specifically, the invention makes it possible to take into account the stability of the absorption of the surface layer. In the method according to the prior art, the variation of the absorption in the deep layer is distributed both in the deep layer and in the surface layer.

FIG. 6D shows:

the real variation [HbO2] in the deep layer: see curve $\Delta$O1 the estimations of the variation of [HbO2] in the deep
   layer without taking into account the variation of pa in
   the surface layer: see curve ΔO2 the estimations of the variation of [HbO2] in the deep
   layer by implementing the invention: see curve ΔO3 the real variation of [Hb] in the deep layer: see curve ΔD1 the estimations of the variation of [Hb] in the deep layer
   without taking into account the variation of pa in the
   surface layer: see curve ΔD2 the estimations of the variation of [Hb] in the deep layer
   by implementing the invention: see curve ΔD3.

Figure 6D:
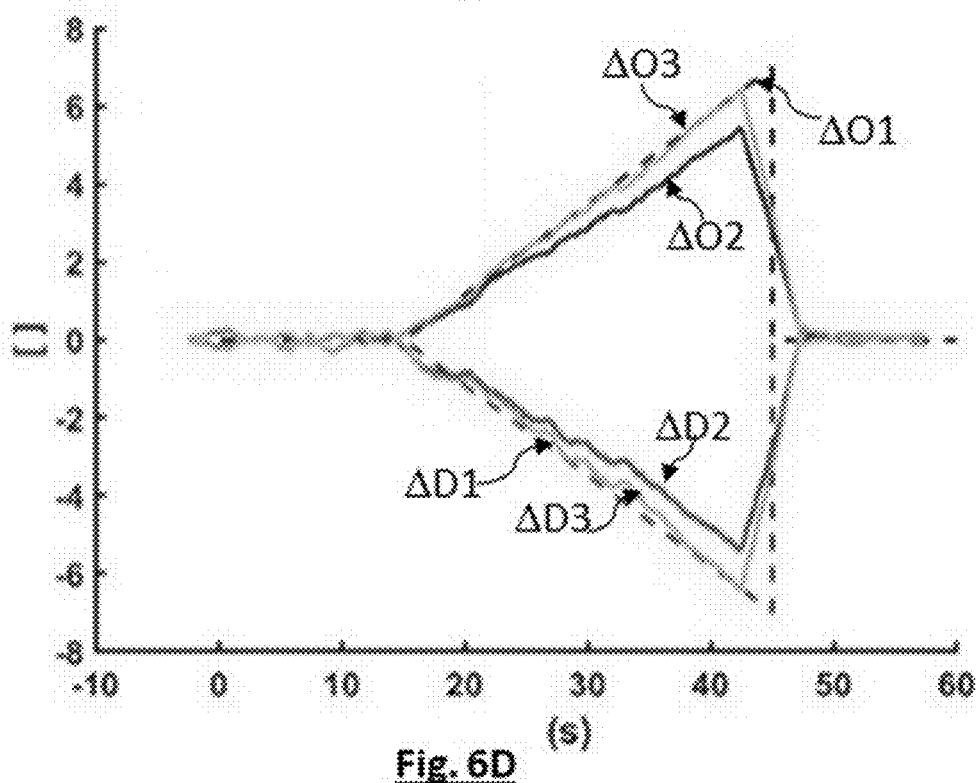

In FIG. 6D, the X axis corresponds to the time (arbitrary
unit) and the Y axis corresponds to the estimated concen-
tration variations.

It can be seen that the curves ΔD3 and ΔO3 are closer to
the real values ΔD1 and ΔO1.

Figure 7A:
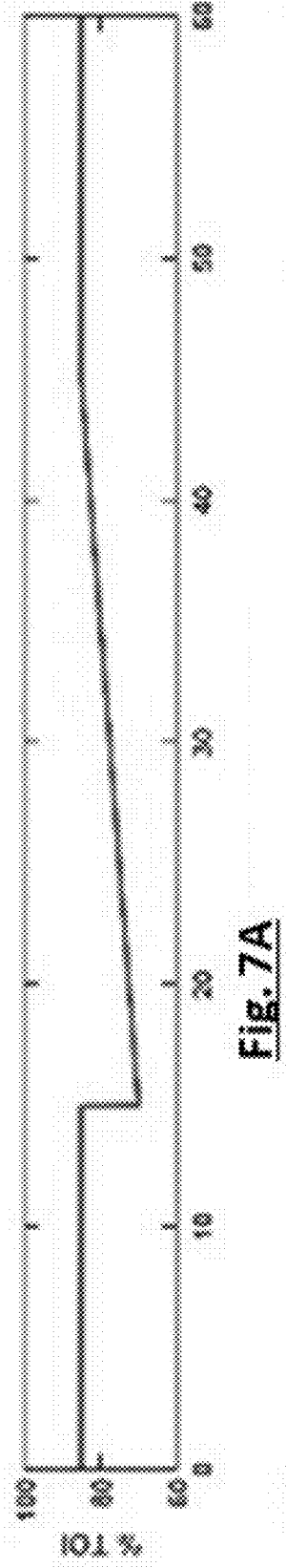
FIGS. 7A to 7D show results obtained, by simulation, by implementing the invention according to a third configuration.
Figure 7B:

According to a third configuration, see FIGS. 7A to 7D,
the oxygenation of the surface layer and the oxygenation of
the deep layer vary (see FIGS. 7A and 7B). In FIGS. 7A and
7B, the X axis corresponds to the time (arbitrary unit) and
the Y axis corresponds to the oxygenation rate defined in
(26).

FIG. 7C shows:

the real profile of [HbO2] in the deep layer: see curve O1 the estimations of [HbO2] in the deep layer without taking
   into account the variation of pa in the surface layer: see
   curve O2 the estimations of [HbO2] in the deep layer by imple-
   menting the invention: see curve O3 the real profile of [Hb] in the deep layer: see curve D1 the estimations of [Hb] in the deep layer without taking
   into account the variation of pa in the surface layer: see
   curve D2 the estimations of [Hb] in the deep layer by implementing
   the invention: see curve D3.

Figure 7C:
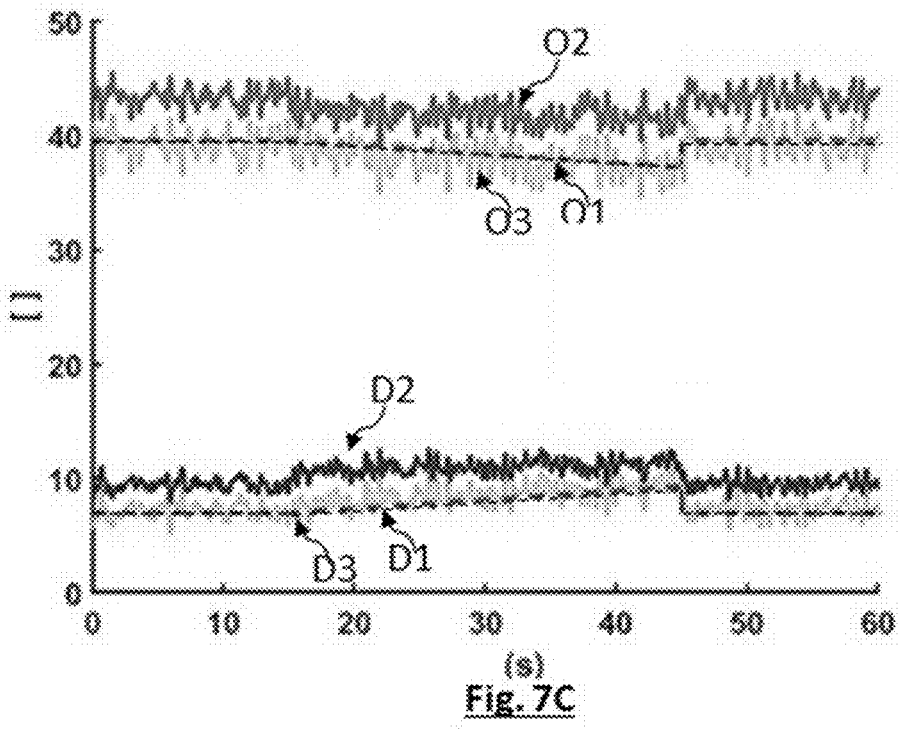

In FIG. 7C, the X axis corresponds to the time (arbitrary
unit) and the Y axis corresponds to the estimated concen-
trations.

It can be seen that the curves D3 and O3 are closer to the
real values D1 and O1.

FIG. 7D shows:

the real variation [HbO2] in the deep layer: see curve ΔO1 the estimations of the variation of [HbO2] in the deep
   layer without taking into account the variation of pa in
   the surface layer: see curve ΔO2 the estimations of the variation of [HbO2] in the deep
   layer by implementing the invention: see curve ΔO3 the real variation of [Hb] in the deep layer: see curve ΔD1 the estimations of the variation of [Hb] in the deep layer
   without taking into account the variation of pa in the
   surface layer: see curve ΔD2 the estimations of the variation of [Hb] in the deep layer
   by implementing the invention: see curve ΔD3.

Figure 7D:
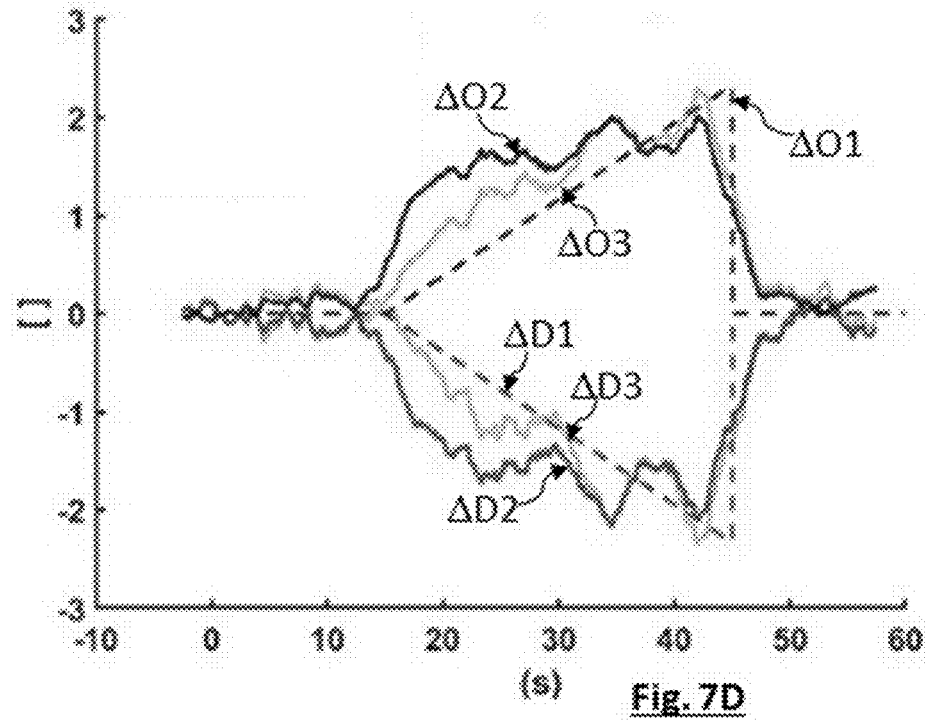

In FIG. 7D, the X axis corresponds to the time (arbitrary
unit) and the Y axis corresponds to the estimated concen-
tration variations.

It can be seen that the curves ΔD3 and ΔO3 are closer to
the real values ΔD1 and ΔO1.

The invention claimed is:

1. A method for determining a variation of absorption
properties of an object, between a first instant and a second
instant later than the first instant, the object being delimited
by a surface, the object comprising a surface layer and a
deep layer, the surface layer extending between the surface
and the deep layer, the method comprising:

a) illuminating the object by a light source, the light
   source emitting an illumination beam forming an illu-
   mination zone on the surface of the object; and b) detecting photons backscattered by the object, after
   being propagated in the object, by a photodetector, the
   detected backscattered photons emanating from a
   detection zone on the surface of the object, the detec-
   tion zone being situated at a detection distance from the
   illumination zone, the detection distance being chosen
   from among, in ascending order:

a first detection distance, forming a first detection zone;

a second detection distance, forming a second detection
   zone;

a third detection distance, forming a third detection zone;

wherein detecting the photons, at the first detection zone,
   at the second detection zone and at the third detection
   zone, generate a detection signal at the first detection
   zone, at the second detection zone and at the third
   detection zone respectively, wherein the method com-
   prises, chronologically:

(i): at the first instant, implementing steps a) and b) by
   detecting the photons in the second and third detection
   zones;

(ii): from the detection signals at the second and third
   detection zones resulting from (i), estimating an
   absorption coefficient of the object, the surface layer
   and the deep layer being considered as having a same
   absorption coefficient;

(iii): from the absorption coefficient resulting from (ii),
   estimating an average distance travelled by the pho-
   tons, within the surface layer, between the illumination
   zone and the first detection zone;

(iv): at the second instant, implementing steps a) and b) by
   detecting the photons backscattered in the first detec-
   tion zone;

(v): from the detection signal at the first detection zone
   resulting from (iv), and the average distance resulting
   from (iii), estimating a variation of the absorption
   coefficient in the surface layer between the first instant
   and the second instant;

(vi): at the second instant, implementing steps a) and b) by
   detecting, in the step b), the photons in the second and
   third detection zones; and (vii): from the detection signals at the second and third
   detection zones resulting from (vi), and the variation of
   the absorption coefficient in the surface layer, resulting
   from (v), estimating the absorption coefficient in the
   deep layer at the second instant.

2. The method of claim 1, wherein the step (i) further
comprises:

from the detection signals measured at the second detec-
   tion zone and the third detection zone, at the first
   instant, determining a spatial variation of the absor-
   bance of the object at the first instant;

from the spatial variation of the absorbance of the object,
   at the first instant, estimating a first estimated absorp-
   tion coefficient in the surface layer and in the deep layer
   at the first instant; and applying a first absorption calibration function to the first
   estimated absorption coefficient, so as to determine the
   absorption coefficient, in the surface layer and in the
   deep layer, at the first instant.

3. Method according to claim 2, wherein the step (vii)
further comprises:

from the detection signals measured at the second detec-
   tion zone and the third detection zone, at the second instant, determining a spatial variation of the absorbance of the object, at the second instant;

from the spatial variation of the absorbance of the object, at the second instant, estimating a first estimated absorption coefficient in the deep layer at the second instant; and applying a second absorption calibration function to the first estimated absorption coefficient in the deep layer at the second instant, so as to determine the absorption coefficient, in the deep layer, at the second instant, the second absorption calibration function taking into account the variation of the absorption coefficient in the surface layer between the first instant and the second instant.

4. The method of claim 3, wherein step (vii) further comprises:

from the variation of the absorption coefficient in the surface layer resulting from (v), estimating an average distance travelled by the photons, in the surface layer, between the illumination zone and the first detection zone, at the second instant;

calculating a ratio between the average distances travelled by the photons resulting respectively from the preceding substep and the step (ii); and using the ratio to form the second absorption calibration function.

5. The method according to claim 3, wherein the method comprises estimating the absorption coefficient, in the surface layer, at the second instant; and the second absorption calibration function is established using modellings or experimental measurements performed on phantoms, each phantom comprising:

a surface layer, the absorption coefficient of which corresponds to the absorption coefficient estimated, in the surface layer, at the second instant; and a deep layer, the absorption coefficient of which is variable between the different phantoms.

6. The method of claim 1, wherein the first detection distance is less than 2 cm; and the second and third detection distances are greater than 2 cm.

7. A device configured to be applied facing a surface of an object during at least one first instant and a second instant, the device comprising:

a light source configured to emit an illumination beam, forming an illumination zone, on the surface of the object;

a photodetector, configured to form a detection signal from a detection of photons backscattered by the object, in;

a first detection zone, extending to a first detection distance from the illumination zone;

a second detection zone, extending to a second detection distance from the illumination zone, the second detection distance being greater than the first detection distance; and a third detection zone, extending to a third detection distance from the illumination zone, the third detection distance being greater than the second detection distance; and at least one processor, programmed to implement a process from detection signals formed by the photodetector, the process including (i): at the first instant, implementing steps a) and b) by detecting the photons in the second and third detection zones, steps (a) and (b) including a) illuminating the object by a light source, the light source emitting an illumination beam forming an illumination zone on the surface of the object;

b) detecting photons backscattered by the object, after being propagated in the object, by a photodetector, the detected backscattered photons emanating from a detection zone on the surface of the object, the detection zone being situated at a detection distance from the illumination zone, the detection distance being chosen from among, in ascending order:

a first detection distance, forming a first detection zone;

a second detection distance, forming a second detection zone; and a third detection distance, forming a third detection zone;

(ii): from the detection signals at the second and third detection zones resulting from (i), estimating an absorption coefficient of the object, the surface layer and the deep layer being considered as having a same absorption coefficient;

(iii): from the absorption coefficient resulting from (ii), estimating an average distance travelled by the photons, within the surface layer, between the illumination zone and the first detection zone;

(iv): at the second instant, implementing steps a) and b) detecting the photons backscattered in the first detection zone;

(v): from the detection signal at the first detection zone resulting from (iv), and the average distance resulting from (iii), estimating a variation of the absorption coefficient in the surface layer between the first instant and the second instant;

(vi): at the second instant, implementing steps a) and b) by detecting, in the step b), detecting the photons in the second and third detection zones; and (vii): from the detection signals at the second and third detection zones resulting from (vi), and the variation of the absorption coefficient in the surface layer, resulting from (v), estimating the absorption coefficient in the deep layer at the second instant, wherein detection signals include in the step (ii), detection signals at the second and third detection zones;

in the step (v), detection signal at the first detection zone; and in the step (vii), detection signals at the second and third detection zones.

8. The device of claim 7, wherein the first detection distance is less than 2 cm; and the second and third detection distances are greater than 2 cm.

* * * * *